(12) United States Patent
Ishimaru et al.

(10) Patent No.: US 8,137,393 B2
(45) Date of Patent: Mar. 20, 2012

(54) STENT GRAFT INDWELLING DEVICE AND FIXED CHIP

(75) Inventors: Shin Ishimaru, Tokyo (JP); Yoshihiko Yokoi, Tokyo (JP)

(73) Assignees: Kawasumi Laboratories, Inc., Tokyo (JP); Shin Ishimaru, Tokyo (JP)

( * ) Notice: Subject to any disclaimer, the term of this patent is extended or adjusted under 35 U.S.C. 154(b) by 686 days.

(21) Appl. No.: 11/578,287

(22) PCT Filed: Apr. 18, 2005

(86) PCT No.: PCT/JP2005/007737
§ 371 (c)(1),
(2), (4) Date: Oct. 13, 2006

(87) PCT Pub. No.: WO2005/099806
PCT Pub. Date: Oct. 27, 2005

(65) Prior Publication Data
US 2008/0039925 A1 Feb. 14, 2008

(30) Foreign Application Priority Data
Apr. 16, 2004 (JP) .................................. 2004-121229

(51) Int. Cl.
*A61F 1/06* (2006.01)
(52) U.S. Cl. ..................... 623/1.11; 623/1.12; 623/1.13; 623/1.14; 623/1.15
(58) Field of Classification Search ......... 623/1.11–1.14
See application file for complete search history.

(56) References Cited

U.S. PATENT DOCUMENTS

| | | | | |
|---|---|---|---|---|
| 5,035,706 A | * | 7/1991 | Giantureo et al. | 606/198 |
| 5,231,989 A | * | 8/1993 | Middleman et al. | 600/434 |
| 5,366,473 A | * | 11/1994 | Winston et al. | 606/198 |
| 5,639,278 A | * | 6/1997 | Dereume et al. | 623/1.13 |
| 5,674,277 A | * | 10/1997 | Freitag | 623/1.13 |
| 5,702,419 A | * | 12/1997 | Berry et al. | 623/1.13 |
| 5,723,003 A | * | 3/1998 | Winston et al. | 623/1.13 |
| 6,238,430 B1 | * | 5/2001 | Klumb et al. | 623/1.11 |
| 6,280,467 B1 | * | 8/2001 | Leonhardt | 623/1.16 |
| 6,702,802 B1 | * | 3/2004 | Hancock et al. | 604/524 |

(Continued)

FOREIGN PATENT DOCUMENTS

JP 5 81257 11/1993

(Continued)

OTHER PUBLICATIONS

Machine Translation from JPO website of JP 2000350785 A; Dec. 2000; Ishimaru.*

*Primary Examiner* — David Isabella
*Assistant Examiner* — Jacqueline Woznicki
(74) *Attorney, Agent, or Firm* — Oblon, Spivak, McClelland, Maier & Neustadt, L.L.P.

(57) ABSTRACT

A stent graft indwelling device (1) comprising a dilator (10) and a sheath (30) in which the dilator (10) and a stent graft (60) are to be loaded, the stent graft indwelling device (1) having a wire (40) or a fixed chip (20) as means for adjusting the insertion angle and/or indwelling site of the stent graft (60) when the stent graft (60) is released from the sheath (30) in a diseased part by this indwelling device, so that the insertion angle and indwelling site can be finely adjusted in a blood vessel in a semi-expansion state where the stent graft is not completely expanded.

3 Claims, 11 Drawing Sheets

U.S. PATENT DOCUMENTS

2005/0240257 A1 10/2005 Ishimaru et al.

FOREIGN PATENT DOCUMENTS

| JP | 6 505188 | 6/1994 |
| JP | 8 512227 | 12/1996 |
| JP | 2000 262632 | 9/2000 |
| JP | 2000 350785 | 12/2000 |
| JP | 2001 504016 | 3/2001 |
| JP | 2006346350 A | * 12/2006 |

* cited by examiner (A)

(B)

(C)

(D)

(E)

(F)

(A)

(B)

(C)

(D)

(E)

(A)

(B)

(C)

(D)      (E)

STENT GRAFT INDWELLING DEVICE AND FIXED CHIP

TECHNICAL FIELD

This invention relates to a stent graft indwelling device that is designed for reliably indwelling a stent graft, for the treatment of an ecstatic disease (aneurysm), an arterial constrictive diseases or some other diseases at a safe site of a diseased part and that decreases the pains and burdens of a patient and reduces the cost or expenses, and relates also to improvements in a fixed chip to be loaded on a dilator of the stent graft indwelling device.

BACKGROUND ART

The present inventors have proposed, by JPA-2000-262632, a stent graft indwelling device having a catheter, a pushing rod (also called "dilator") and a sheath, in which a swollen portion that has the form, for example, of an ellipsoid, for blocking or sealing a leading end of the sheath is provided in the vicinity of the leading end of the catheter and the swollen portion is provided with an engagement means such as a notch or the like so that a hook attached to the leading end of a stent unit can be removably engaged therewith.

In JP-A-2000-350785, further, the present inventors have proposed a stent graft indwelling device having a dilator composed of a base body portion, a stent graft holding portion and a head portion and a sheath loadable with the dilator, in which the head portion is shaped in the form of a semi-ellipsoid or a semi-sphere and is partly projected from the leading end of the sheath for blocking or sealing the leading end of the sheath, that part of the head portion inside the sheath is provided with an engagement means such as a notch or the like such that a hook attached to the stent is removably engaged therewith and one or a plurality of contrast medium delivery channel(s) and a guide wire guiding channel are provided in the above dilator.

The above proposed stent graft indwelling devices have the following novel features.

That is, (a) it is ensured that safe and reliable indwelling of the stent graft is made even in an intracorporeal organ such as an extremely curved blood vessel, etc., and reducing the pains and burdens of a patient. (b) The entering of a body fluid such as arterial blood into a stent graft portion held in the sheath can be prevented, and the stent graft held in the sheath can be safely delivered into an intracorporeal tubular member such as a blood vessel (artery) without damaging the inner wall thereof. (c) When the catheter is inserted into an intracorporeal tubular member such as blood vessel while a contrast medium is ejected from a contrast medium ejecting port, the insertion site of the catheter can be monitored by image, and when the catheter is moved forward and backward while the contrast medium is ejected from the contrast medium ejecting port, thereby enabling a image-wise spotting of a safety site in a diseased part of the intracorporeal tubular member such as a blood vessel in a short period of time. Therefore, the insertion of the stent graft housed in the sheath into the intracorporeal tubular member such as a blood vessel and the determining of indwelling position of the stent graft are safe and easy. (d) When the stent graft is pushed out of the sheath and self-dilated in a pre-determined indwelling or placement position in an intracorporeal tubular member such as a blood vessel, the shifting of the stent graft caused by the pressure of a body fluid such as a blood flow is prevented. (e) The stent graft can be broadened in application to the treatment of aneurysm, etc., to which no conventional stent grafts have ever been applied, thereby a beneficial treatment method for many patients with aneurysm, etc., can be provided. (f) The stent graft is also provided with effects that ensure direction of the curvature-based stent graft design and the like.

These stent graft indwelling devices that have been proposed have the above excellent features and produce remarkable advantageous effects as compared with conventional devices.

However, unfortunately, these stent graft indwelling devices have a so-called one-piece structure in which the dilator is formed integrally with its head portion (called a swollen portion or fixed chip portion as well) of the dilator. Thereafter, the present inventors have found it desirable to ensure that the stent graft does not rotate in the sheath, that it does not move forward or backward and that it does not come off the dirator when it is housed in the sheath. Further, it has been found that when the stent graft is to be released from the sheath, it is desirable that the stent graft should come off easily and without any resistance. However, it is difficult to overcome these problems with the structure of the above-described dilator head.

Further, the dilator has the head portion whose swollen portion has a greatly expanded form like a spindle as compared with a holding portion (for example, see FIG. 2 of JP-A-2000-350785), so that it has been not easy to process a metal mold for integrally molding the dilator with an injection machine or the like. In actual medical care facilities, therefore, a craft man produces each dilator with swollen portion by piece by piece cutting work followed by thermal processing, etc., and the production thereof takes time. It has been also found that products vary in form.

The following problems have been also found. In the above stent graft indwelling device, the form of the above swollen portion of the dilator is fixed, so that it is not always possible that the sheath be inserted at a constant angle to the form of a blood vessel when inserting the sheath. And hence the stent graft is released into a blood vessel while it is dilated unit by unit, so that it is difficult to finely or precisely adjust the exact position and fixing angle of the above stent graft. Further, the blood vessel size and the degree of curvature thereof differ depending upon individual patients, and when these stent graft indwelling devices are used for a patient having an extremely or excessively curved blood vessel or for a patient having a boss in the distal arc portion of a thoracic aorta, it has not been necessarily easy to safely place the released stent graft.

That is because, when the stent graft is to be placed or in the center (heart) side rather than in a nutrient canal branch portion of a captu-cervical part in the arc portion of an aorta, it is the most important object to make sure that the contact of the stent graft base body and the leading end of the sheath to the greater curvature side of the arc portion of the thoracic aorta be minimized for preventing complications such as cerebral infarction.

In view of the importance of the problems associated with conventional stents, the present inventors have made diligent studies for providing a stent that is remarkably improved in safety and a tracking property during its delivery in the artery and in long-term stable indwelling in a diseased part, and have arrived at this invention.

DISCLOSURE OF THE INVENTION

The present invention has been made from the above viewpoint, and according to this invention, the following inventions are provided.

[1] A stent graft indwelling device (1) comprising a dilator (10) having a stent graft holder (14) and a sheath (30) in which is loaded a stent graft (60) held on the stent graft holder (14) of said dilator (10) wherein, the stent graft indwelling device (1) having means for adjusting the insertion angle and/or the indwelling site of said stent graft (60) when said stent graft (60) is released from said sheath (30) for indwelling.

[2] A stent graft indwelling device (1) comprising a dilator (10) having provided with a fixed chip (20) and a sheath (30) in which is loaded a stent graft (60) held on the stent graft holder (14) of said dilator (10), characterized in that said stent graft (60) per se is curved by harnessing the expansion power of the stent graft (6) to make the fixed chip (20) free from the wall of a blood vessel when said stent graft (60) is released from said stent graft indwelling device (1) for indwelling, thereby reducing and decreasing damage on the blood vessel and the disengagement of a thrombolic substance from the blood vessel wall.

[3] The stent graft indwelling device (1) as recited in [1] or [2], wherein the means for adjusting the insertion angle and/or the indwelling site of the stent graft (60) includes a wire (40) and/or a fixed chip (20).

[4] The stent graft indwelling device (1) of any one of [1] to [3], wherein said dilator (10) has a base body portion (11), a stent graft holding portion (14) and the fixed chip (20).

[5] The stent graft indwelling device (1) of any one of [1] to [4], wherein said dilator (10) has a fluid passage (17, 18) formed along a side face of the base body portion (11).

[6] The stent graft indwelling device (1) of any one of [1] to [5], wherein said dilator (10) has a wire fixing portion (43) or wire fixing notch portion formed on a fore portion of the base body portion (11).

[7] The stent graft indwelling device (1) of any one of [1] to [6], wherein a wire fixing member (15) is mounted on a proximal end portion (12) of said dilator (10).

[8] The stent graft indwelling device (1) of any one of claims 1 to 7, wherein said stent graft (60) is constituted of a plurality of tubular units (61) that are connected in the central axis direction thereof, a holding ring (69) and a hook portion (66) are attached to an outer circumference of a forward end of the first annular unit (61) and holding rings (67, 68) are also attached to said hook portion (66).

[9] The stent graft indwelling device (1) of any one of [2] to [8], wherein said fixed chip (20) is constituted of a base body (21) and a cap (22) and a hook holding groove (26) is formed between said cap (22) and an upper opening portion of the base body (21).

[10] The stent graft indwelling device (1) of any one of [3] to [9], wherein said wire (40) is extended from an inside of the stent graft (60) to the wire fixing member (15) formed in the proximal end portion (12) of the dilator and fixed, either through a fluid passage (17, 18) between an outer circumference of the dilator (10) and an inner surface of the sheath (30) and the proximal end portion of the base body portion (11) or through a wire lumen (100) formed from the leading end of the dilator (10) to the proximal end portion (12) and a wire withdrawal outlet (19), and the thus fixed wire (40) is to work to exert tension, thereby decreasing the stent graft (60) in length when the stent graft (60) is released from the sheath (30), and an adjustment of the release angle and indwelling position of the stent graft (6) is made when the stent graft (60) is released.

[11] The stent graft indwelling device (1) of any one of [1] to [10], which has a constitution in which the wire end portion (41) fixed in said fixing member (15) is unfixed or loosened and drawn out of the holding rings (67, 68, 69) of said stent graft (60) whereby the wire (40) can be drawn out of said stent graft indwelling device (1).

[12] The stent graft indwelling device (1) of any one of claims 2 to 11, wherein the forward end of the stent graft holding portion (14) is forced into a lumen (24) of proximal end portion (23) of said fixed chip base body (21) and a lumen (25) of a cap (22) and said forward end of the stent graft holding portion (14) is thereby passed through these lumen (24) of the base body and lumen (25) of the cap to fix the cap (22) and the base body (21) together.

[13] The stent graft indwelling device (1) of any one of [1] and [3] to [12], wherein said means for adjusting the insertion angle and/or indwelling site of the stent graft (60) includes the base portion (11), stent graft holding portion (14) and fixed chip (20) of said dilator (10), the wire fixing member (15) mounted on the proximal end portion (12) of the dilator; the hook portion (66) and holding rings (67, 69, 69) formed on the forward end of the first tubular unit (61); and the wire (40) that extends from said holding rings (67, 68, 69) through between the dilator (10) and the sheath (30) or through a wire lumen (100) formed all the distance from the forward end of the dilator (10) to the proximal end portion (12) of the dilator and further extended through the wire withdrawal outlet (19) and is fixed in said wire fixing member (15).

[14] A stent graft (60) that is to be loaded in a dilator (10) of a stent graft indwelling device (1), that is constituted of a plurality of tubular units (61) that are connected in the central axis direction thereof, wherein a holding ring (69) and a hook portion (66) are attached to an outer circumference of forward end of the first tubular unit (61) and holding rings (67, 68) are also attached to said hook portion (66).

[15] A fixed chip (20) to be attached to a dilator (10) of a stent graft indwelling device (1) constituted of a base body (21) and a cap (22), wherein a hook holding groove (26) is formed between the cap (22) and an upper opening portion of the base body (21).

In Figures, numeral 1 indicates a stent graft indwelling device, 10 indicates a dilator, 11 indicates a dilator base body portion, 12 indicates a dilator proximal end portion, 13 indicates a contrast medium injection port, 14 indicates a stent graft holding portion or stent graft holder, 15 indicates a wire fixing member, 16 indicates a lumen (e.g., a lumen for a guide wire or contrast medium injection), 17 indicates a fluid passage (concave portion), 18 indicates a fluid passage (chamfered cut portion), 19 indicates a wire withdrawing outlet, 20 indicates a fixed chip, 21 indicates a fixed chip base body, 22 indicates a cap for a fixed chip, 22A indicates a cap sleeve portion, 23 indicates a fixed chip base body proximal end portion, 24 indicates a base body proximal end lumen, 25 indicates a cap lumen, 26 indicates a hook holding groove or mechanism, 27 indicates a contrast medium ejecting port, 28 indicates a cap top portion, 29 indicates a cap engagement portion, 30 indicates a sheath, 31 indicates a hub, 32 indicates a liquid inlet, 37 indicates a hub cap with a valve, 38 indicates an opening portion, 39 indicates a large-diameter portion, 40 indicates a wire, 41 indicates a wire end portion, 42 indicates a wire end portion, 43 indicates a wire fixing portion (wire fixing notch portion), 45 indicates a flexed portion of the wire 40, 50 indicates a catheter, 60 indicates a stent graft, 61 indicates a tubular unit, 62 indicates a flexed portion of the stent 64, 63 indicates a connecting portion, 64 indicates a stent, 65 indicates a tubular member (graft), 66 indicates a hook or hook portion, 67 indicates a holding ring of the hook portion, 68 indicates a holding ring of the hook portion, 69 indicates a holding ring and 100 indicates a wire lumen.

PREFERRED EMBODIMENTS OF THE INVENTION

This invention will be explained in detail below with reference to the drawings.
(Stent Graft Indwelling Device)

Figure 9:
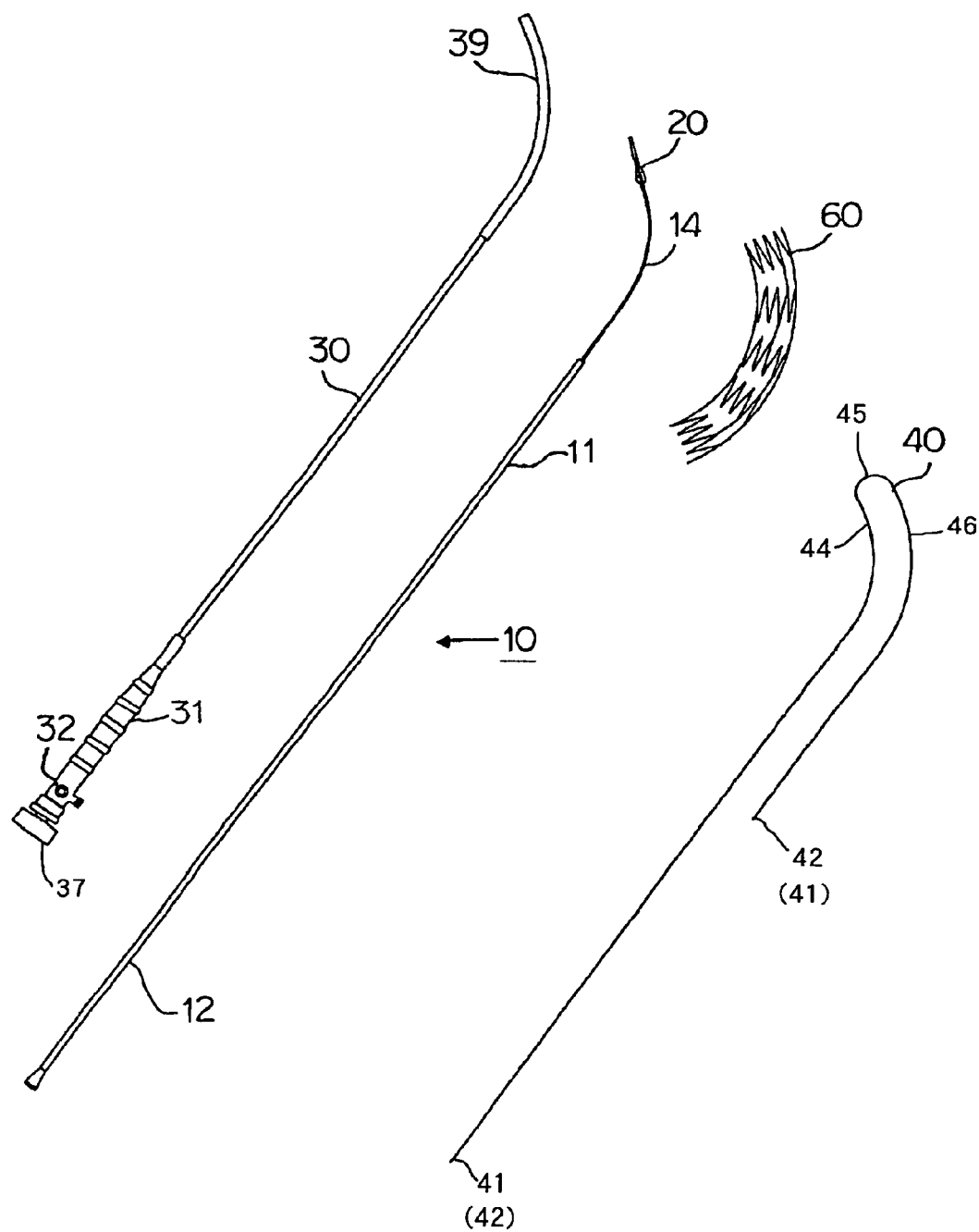
FIG. 9 is an exploded view of the stent graft indwelling device of this invention and shows that said device comprises the dilator 10, the sheath 30, a stent graft 60 and a wire 40.

As shown in the exploded view of FIG. 9, the stent graft indwelling device 1 of this invention is an indwelling device comprising a dilator 10 having a stent graft holder 14 and a sheath 30 to be loaded with a stent graft 60 held on the stent graft holder 14 of the above dilator 10, and the stent graft indwelling device 1 is characterized in that the device have means for adjusting the insertion angle and/or indwelling site or place of the above stent graft 60 when the above stent graft 60 is released from the above sheath 30 and placed at the site.

And, the means for adjusting the insertion angle and/or indwelling site of the above stent graft 60 is realized preferably by a wire 40 and/or a fixed chip 20 mounted on the dilator 10.

As shown in FIG. 9, the feature of the indwelling device of this invention is that it is the stent graft indwelling device 1 having the dilator 10 having the fixed chip 20 and the sheath 30 loaded with the stent graft 60 held on the stent graft holder 14 of the above dilator 10 and that while the stent graft 60 is released from the stent graft indwelling device 1 and placed, the stent graft 60 itself becomes flexed through its own expanding power of the stent graft 60 thereby making the above chip 20 free from a blood vessel wall, and whereby decreasing the damage to the blood vessel and also reducing the disengagement of a thrombolic substance from the blood vessel, as will be described later.

The "means for adjusting the insertion angle and/or indwelling site of the above stent graft 60" refers to the wire 40 and/or the fixed chip 20 in a broad sense as explained above. More specifically, the "means for adjusting the insertion angle and/or indwelling site of the above stent graft 60" refers to the fixed chip 20 mounted on the leading end of the holding portion of the dilator 10 having a base body portion 11, the stent graft holder 14 and the holding portion as shown in FIG. 9, and the wire 40 that is extended through a wire fixing member 15 mounted on the proximal end 12 of the above dilator shown in FIG. 1, a hook portion 66 and holding rings 67, 68 and 69 formed in the forward end portion of a first tubular unit 61 of the stent graft 60 shown in FIGS. 10 and 11, that is also extended from the above holding rings 67, 68 and 69 through between the dilator 10 and the sheath 30 or through a wire lumen 100 formed all the distance from the leading or forward end of the dilator 10 to the proximal end portion 12 of the dilator shown in FIG. 4, and that is further extended through a wire withdrawal outlet 19 and is fixed to the above wire fixing member 15.
(Dilator 10)

The dilator 10 is shown in FIG. 9 as described above and has the base body portion 11, the stent graft holder or stent graft holding portion 14 and the fixed chip 20. The stent graft holder 14 has a smaller diameter than the base body portion 11 for mounting the stent graft 60 on the outer circumference thereof.

The above base body portion 11 and the stent holder 14 are formed from a SUS pipe (rod or bar) or a rigid material such as a hard resin.

Figure 12:
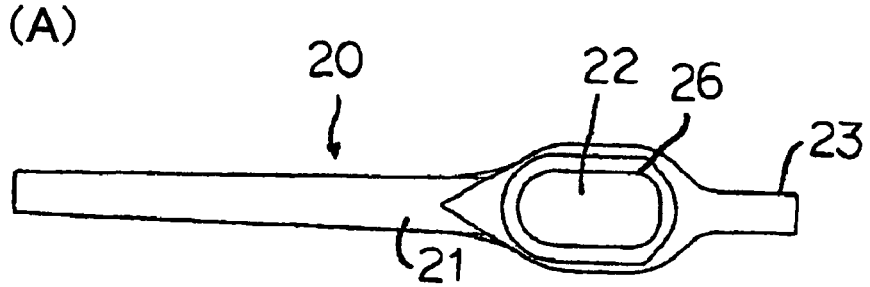
FIGS. 12, 13 and 14 are schematic drawing for explaining the fixed chip 20 in this invention.
Figure 12:
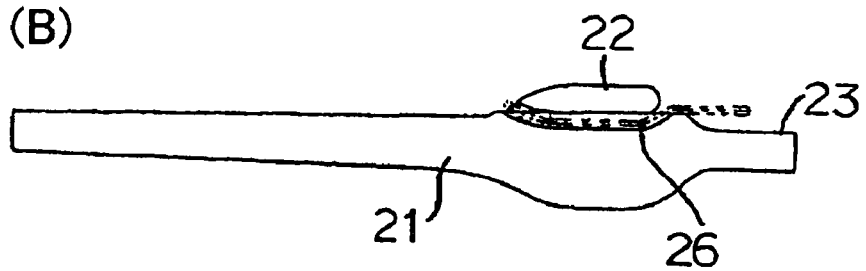
Figure 12:
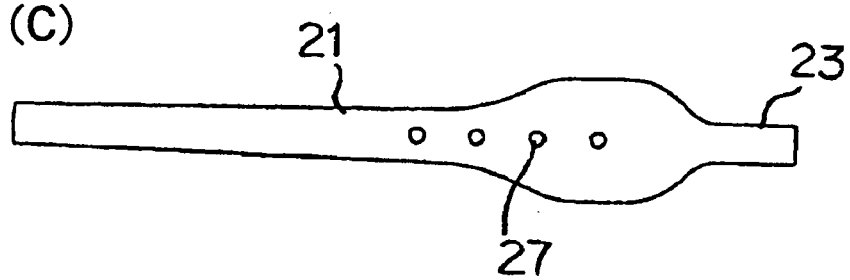
Figure 12:
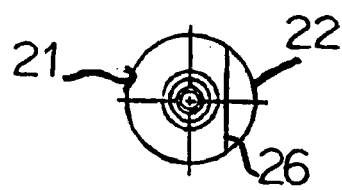
Figure 12:
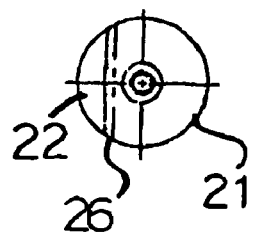
Figure 12:
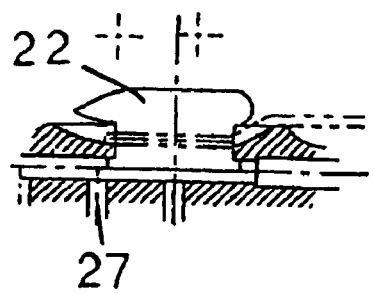
Figure 13:
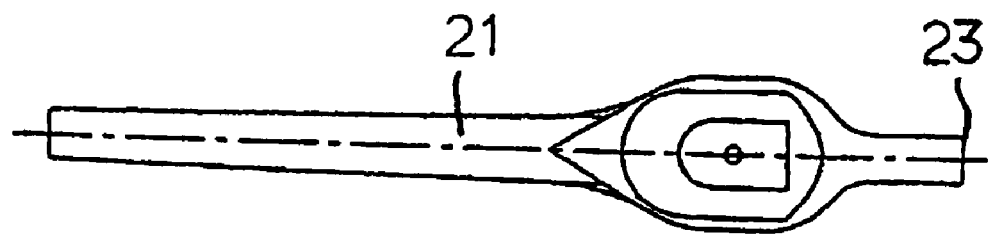
Figure 13:
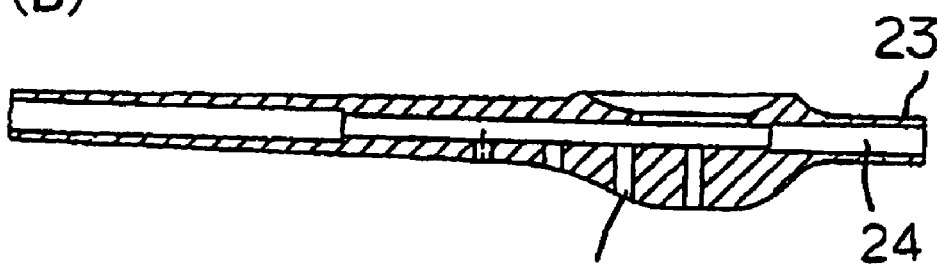
Figure 13:
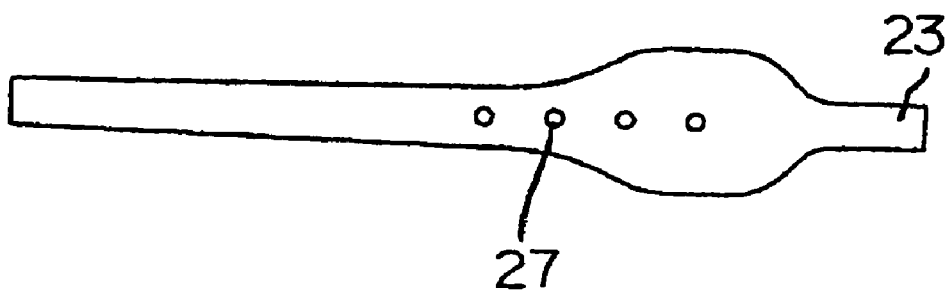
Figure 13:
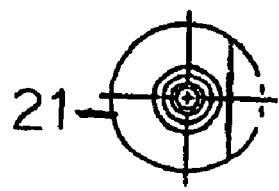
Figure 13:
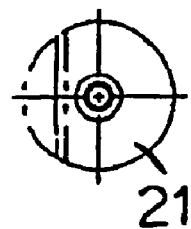
Figure 14:
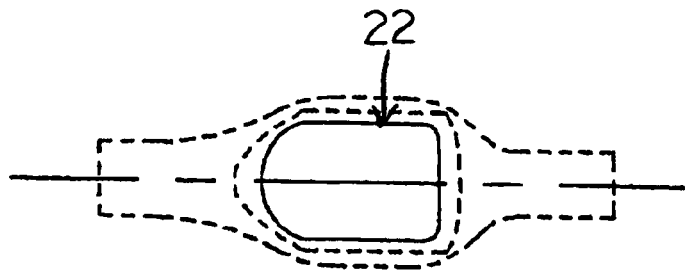
Figure 14:
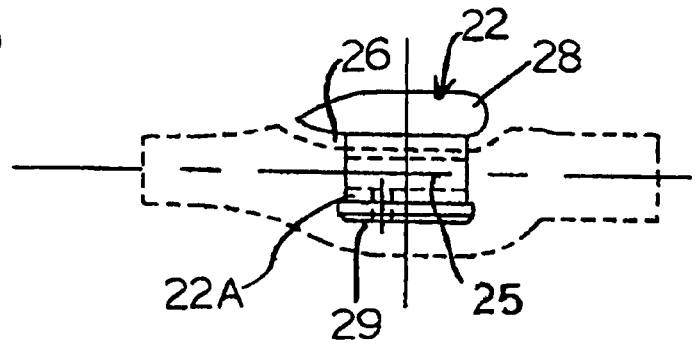
Figure 14:
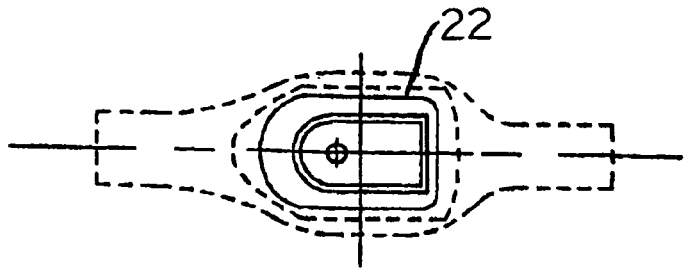
Figure 14:
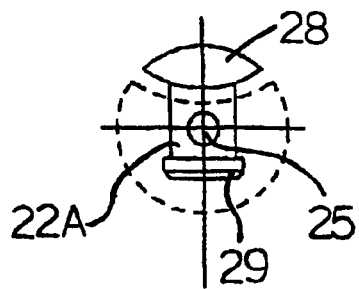
Figure 14:
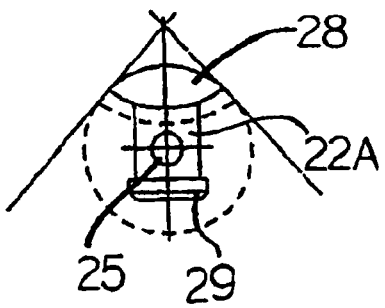

Further, the fixed chip 20 is attached to the leading end of the above stent graft holder 14. As will be described later, the above chip 20 has forms as shown in FIGS. 12 to 14 and is formed from a material having proper hardness or rigidity and flexibility, selected from synthetic resins such as polyamide elastomers, polyurethane, polyvinyl chloride, and the like.

Figure 2:
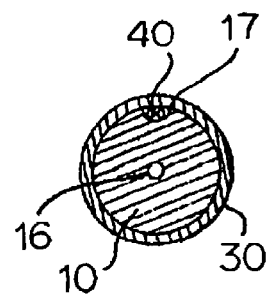
FIG. 2 is an enlarged transverse cross-sectional view taken along A-A line in FIG. 1.
Figure 3:
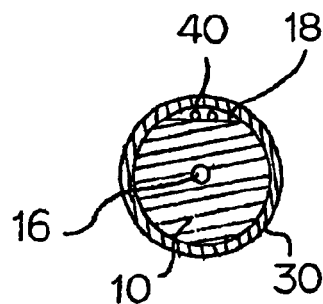
FIG. 3 is another enlarged transverse cross-sectional view taken along A-A line in FIG. 1.

While the dilator 10 is, in principle, constituted of a solid rod, the whole portion of it is not completely solid. On the circumference of the base body portion 11, a fluid passage (empty duct) is formed in the form of a concave portion 17 as shown in FIG. 2, or a fluid passage (empty duct) such as a chamfered cut portion 18 or the like is formed as shown in FIG. 3. Since the dilator 10 having these fluid passages formed thereon, the sheath 30 can be deaerated by letting a saline solution in these passages before inserting the indwelling device intracorporeally. Further, through the fluid passages the guide wire can be inserted, or a contrast medium (imaging agent) can flow.
(Wire Fixing Member)

Figure 6:
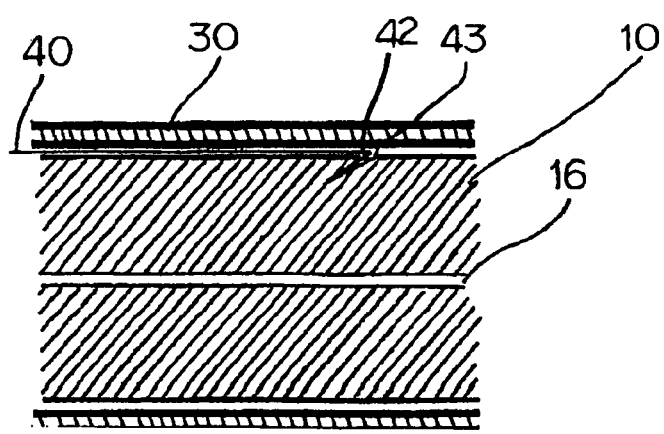
FIG. 6 is an enlarged longitudinal view taken along D-D line in FIG. 6.
Figure 7:
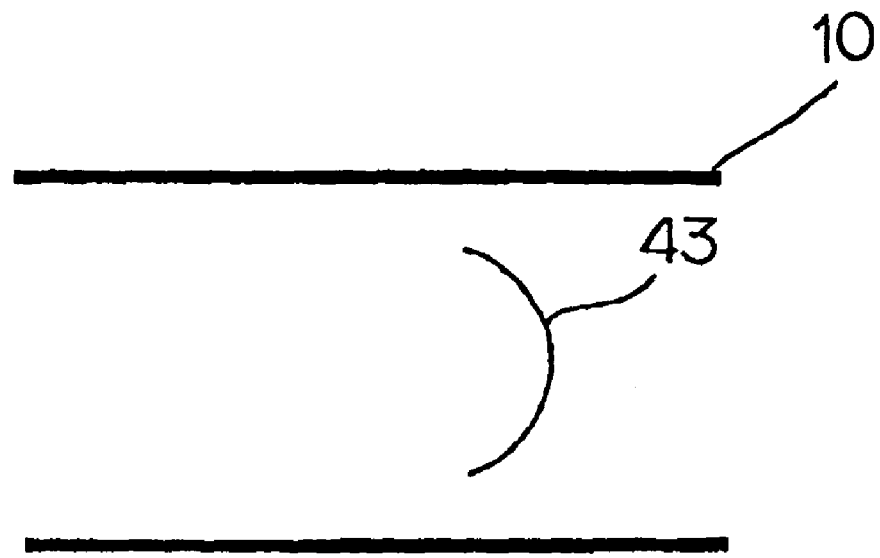
FIG. 7 is a schematic drawing of a notch portion (wire fixing portion) on the surface of the dilator in FIG. 1.
Figure 8:
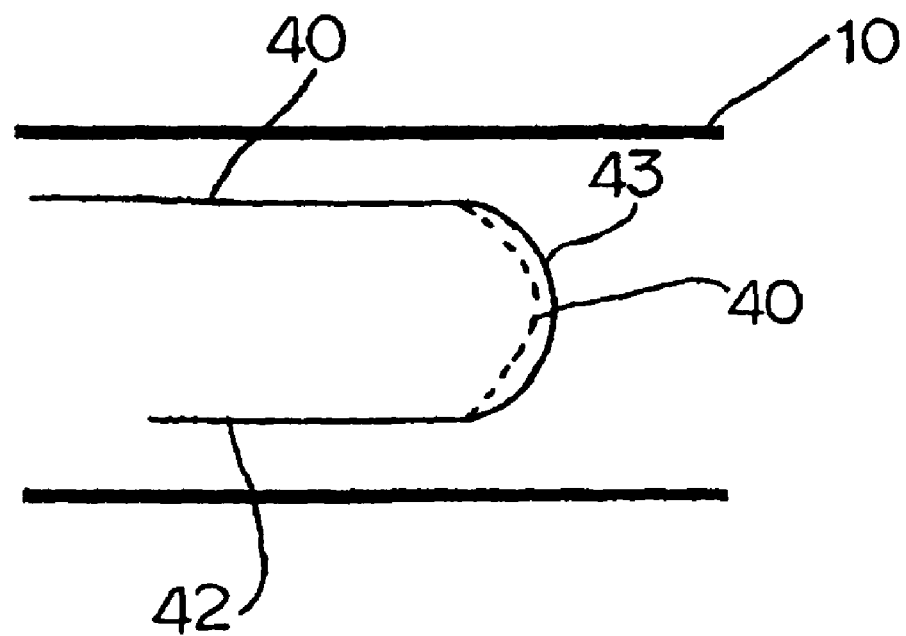
FIG. 8 is a drawing for explaining a state where a wire end portion 42 is fixed with a wire fixing portion 43.

A wire fixing portion 43 (wire fixing notch) is provided on the surface of the fore or forward part of the base body portion 11 of the dilator 10 as shown in FIG. 7. That is, as shown in FIG. 6 (enlarged longitudinal cross-sectional view taken along D-D line in FIG. 1), for the wire 40 having the form show in FIG. 9, the wire fixing portion 43 (wire fixing notch) is provided for one end portion 42 (the portion inside the sheath 30 and is covered by the sheath) of the wire 40, and the wire end portion 42 is inserted into the above fixing notch portion 43 and pushed or pinched in the notch portion 43, thereby securing or fixing the wire end portion 42. FIG. 8 shows a state wherein the wire end portion 42 is pinched and fixed in the notch portion. The form of wire fixing portion 43 is not specially limited so long as it can pinch and fix the wire end portion 42 therein.

Figure 1:
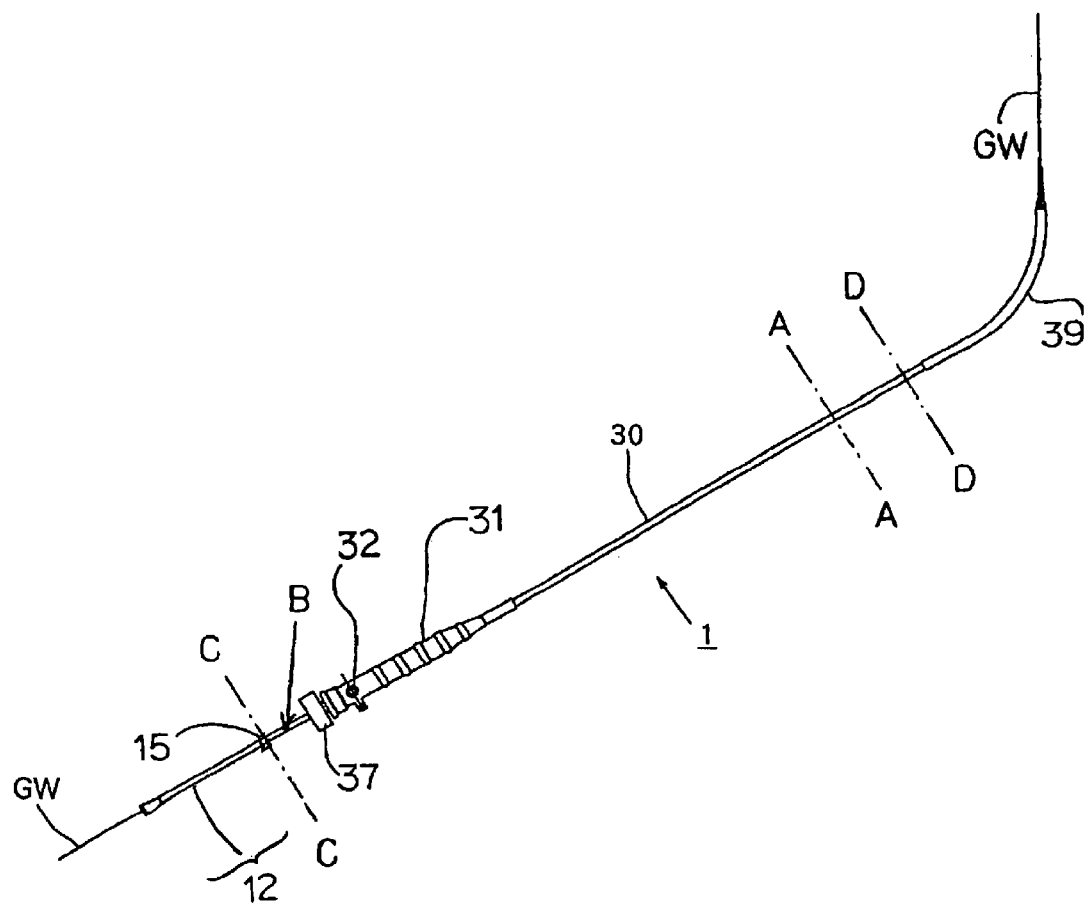
FIG. 1 is a schematic drawing of the stent graft indwelling device of this invention.
Figure 5:
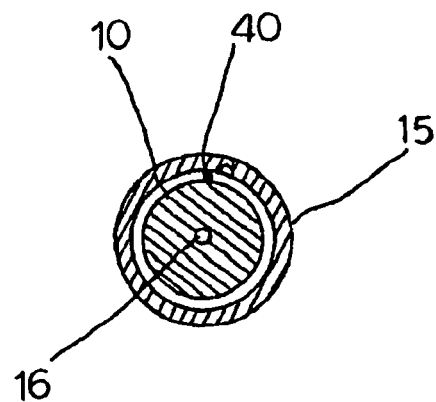
FIG. 5 is an enlarged transverse cross-sectional view taken along C-C line in FIG. 1.

Further, the other end portion 41 (the portion outside the sheath) of the wire 40 is fixed to the proximal end portion 12 of the dilator 10 with a wire fixing member 15 as shown in FIGS. 1 and 5. The wire fixing member 15 refers to a member that can fix or secure the proximal end portion 12 of the dilator 10 and the wire end portion 41 to each other by a pinching pressure and that can release the pinching pressure when it is intended to loose the fixing of the wire end portion 41. Specific examples of the wire fixing member 15 include a well known clamp, a tubular body that is openable and closable with a hinge and a tubular body having a slit formed from a flexible resin material. However, the wire fixing member 15 is not critical so long as it has the above function.

FIG. 5 is an enlarged transverse cross-sectional view taken along C-C line (the position of the wire fixing member) in FIG. 1, and it shows a state wherein the wire 40 is pinched between the wire fixing member 15 and the dilator 10. The position for mounting the wire fixing member 15 on the proximal end portion 12 of the dilator 10 is not firmly fixed or determined, and the wire fixing member 15 may be mounted in a proper position near the wire end portion 41 as required.

Figure 4:
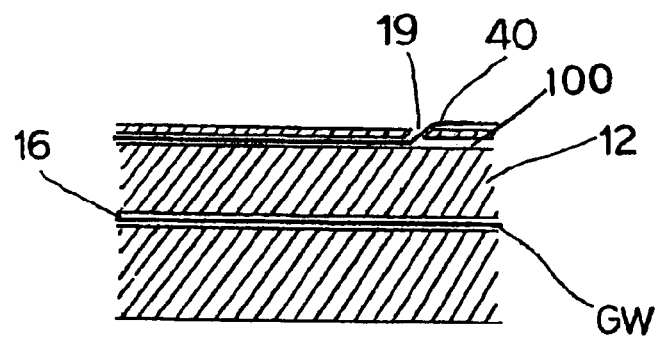
FIG. 4 is a longitudinal cross-sectional view of that portion of a proximal end portion B in FIG. 1 which is around a portion indicated by an arrow mark.

Further, as is shown in FIG. 4, when the wire lumen 100, through which the wire 40 to extend, is formed along all the distance from the leading end portion of the dilator 10 to the proximal end portion 12 of the dilator 10, the wire 40 is caused to come out on the surface side of the proximal end portion 12 of the dilator 10 through the wire withdrawal outlet 19 and fixed on the wire fixing member 15.

(Sheath)

The sheath 30 is formed of a tube having such an inner diameter that the sheath 30 can house or accommodate the above dilator 10 and the stent graft 60 (more specifically, the dilator 10 holding the stent graft mounted on the stent graft holder 14) as shown in FIG. 9. Further, a hub 31 is mounted on the proximal end portion of the sheath 30, and the hub 31 is provided with a liquid inlet 32. On the other hand, a large-diameter portion 39 is formed in the leading end portion of the sheath 30, and the stent graft held on the stent graft holder 14 is arranged inside the large-diameter portion. The sheath 30 is formed from a flexible material. As a flexible material, there can be used, for example, synthetic resins such as a fluorine resin, a polyamide, a polyamide elastomer, polyvinyl chloride and the like or the compounds or multi-layered structures of these resins. Further, composite materials of these resins with metal wire or the like also can be used.

As shown in FIG. 1, a hub cap 37 with a valve is mounted on the base portion of the hub 31 in order to make sure that no blood leaks when the dilator 10 is inserted into the sheath 30.

(Stent and Stent Graft)

The stent graft 60 in this invention is a grafted stent formed by covering a stent 64 with a tubular member (graft) 65 formed of a synthetic resin or the like. Like a stent, the stent graft is used for repairing a blood vessel that suffers damage such as stenosis or aneurysm or as a substitute for a hollow organ such as an artificial vessel or the like.

Figure 10:
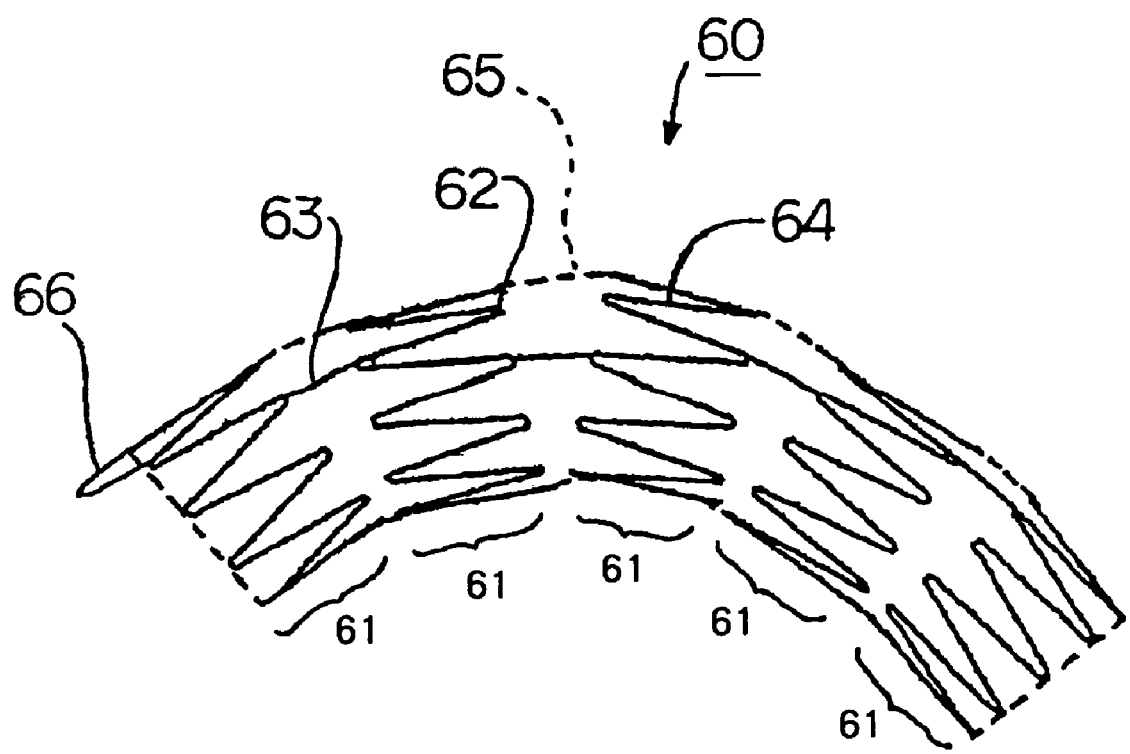
FIGS. 10 and 11 are schematic drawings of a stent graft for use in this invention.

As the stent 64 that constitutes the structure or framework of the stent graft 60 for use in this invention, for example, a stent shown in FIG. 10 is used. The stent 64 as is shown in FIG. 10 is obtained by bending a metal wire in a zigzag form to prepare a tubular (annular) unit 61 formed of zigzag patterns, arranging a plurality of such tubular units 61 in the form of a tubular circumference so as to surround the central axis of the stent, connecting each of the tubular units at least in one place each by known means such as welding, soldering or calking to prepare tubular units 61, 61, 61, . . . and connecting a plurality of such annular units through connecting portions (connecting lines) 63 in the central axis direction of the annular product.

The stent graft is a graft material wherein the outer circumference of the above stent is covered with the flexible tubular member (graft) 65 (e.g., Dacron fiber (polyethylene terephthalate fiber, trade name of Du Pont de Nemours, Co., Ltd.) or a film formed of a fluorocarbon resin such as PTFE (polytetrafluoroethylene) as described above. The above tubular member (graft) 65 is sutured and fixed to flexed portions 62 of leading and trailing ends of the stent 64, for example, with a wire such as a blood vessel suture.

The base material for the metal wire that forms the stent 64 is not specially limited, and it can be selected for use from generally used materials which include: stainless steel such as SUS316L, etc., superelastic alloys such as Ti—Ni alloy, etc., titanium, titanium alloy, tantalum, tantalum alloy, platinum, platinum alloy, tungsten, tungsten alloy and the like.

As the above stent graft 60, there can be preferably used a stent graft having the form proposed by the present inventors in JP-A-2003-334255. However, the stent graft 60 shall not be limited thereto, and there may be used any form of stent graft, that has, at least the form shown in FIG. 10 or any other form constituting a stent framework structure such as a mesh form, of a spiral form etc.

The stent graft preferably used in this invention is of the type which in a non-insertion state, i.e., in an ordinary or pre-use state, has a form curved along the longitudinal direction of the stent as shown in FIG. 10 so as to correspond to the form of a blood vessel into which it is to be inserted. For inserting the stent graft into the sheath 30, it is contracted or compressed in the central axis direction of the stent 64 forming a framework structure, and in the sheath, it is housed or accommodate, in the form of a curve, along the large-diameter portion or the stent graft holder. And, the stent graft housed in the sheath in a curved form or curved state, is delivered to a diseased site together with the sheath and there it is released from the sheath. After released, the stent expands outwardly in the radius direction to come to hold the curved form along the longitudinal direction, the ordinary pre-use state of the stent, which will be discussed with reference to FIG. 18.

The curved-form stent graft (stent as a framework structure) shown in FIG. 10 can be obtained as a three-dimensionally curved form along the longitudinal direction by changing or shifting the positions of the connecting portions 63 between the tubular units 61.

The stent graft 60 has, as its framework structure, the stent 64 that has and perform a spring action and is highly flexible, and the flexible framework structure of the stent 64 is covered with the tubular member 65 formed of a fibrous or film-like synthetic resin as described above, thereby the stent graft can follow the three-dimensional curve of a blood vessel as required.

Figure 11:
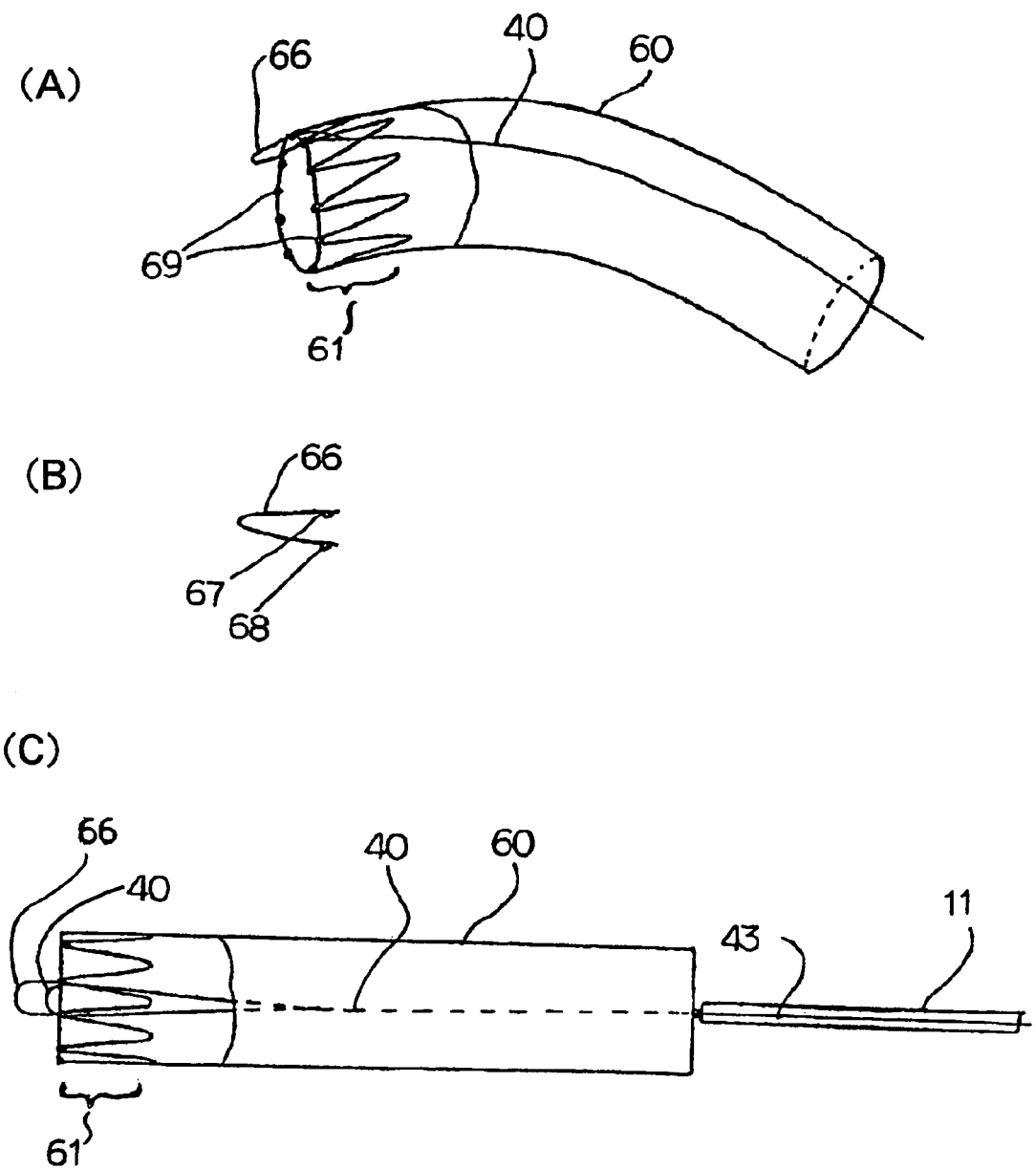

As shown in (A), (B) and (C) of FIG. 11, a plurality of holding rings 69 and one hook portion 66 are attached to the circumference of the leading end of the tubular unit 61 positioned in the first place (from the insertion direction toward a patient) of the stent graft 60 (stent 64), and further, two holding rings 67 and 68 are attached to the hook portion 66.

Each of the holding rings 67 and 68 and the holding rings 69 has the form of a small circle through which the wire 40 can pass. The above holding rings 69 may be formed in the form of a small circle each by rounding each flexed portion 62 of the stent 64 as shown in FIG. 10 forming the forward end of the stent 64 or by rounding a wire (not shown) such as a suture in the form of a small circle. Each of the holding rings 67 and 68 is made by rounding a metal wire or the like in the form of a small circle.

The hook portion 66 is formed in the form of a loop as shown in FIG. 11 and can be made, for example, of a metal wire.

The holding rings 67, 68 and 69 and the hook portion 66 may be formed from a material (wire material) that is the same as, or different from, that used for the stent 64.

Figure 18:
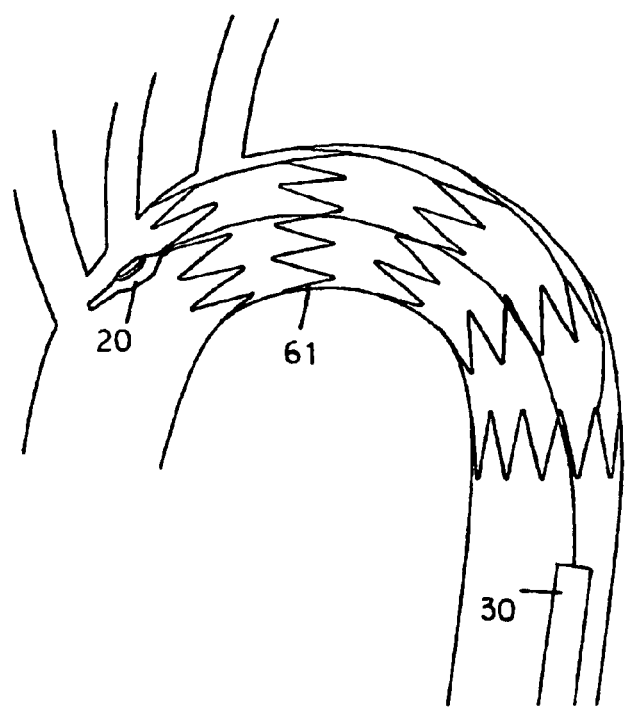

In the stent graft 60 shown in (A) and (B) of FIG. 11, generally, the entire surface of the framework structure of stent 64 is covered with the tubular member or material 65. However, in case when the outer circumference of the stent graft 60 comes in contact with the position of a branch blood vessel as shown in FIG. 18 as will be discussed later, the tubular member 65 of the stent graft 60 is partly cut in the form of a U or V letter thereby exposing part of the stent framework structure to make sure that the branch blood vessel is not blocked.
(Wire)

This invention has a characteristic feature in that the wire 40 is used and the adjustments of the indwelling position (placement position) and insertion angle of the stent graft 60 are made by adjusting the tension on the wire.

As shown in FIG. 9, in principle, the wire 40 has a constitution in which its portion starting from its end portion 41 and corresponding to the base body portion 11 of the dilator forms a straight-line portion that is in parallel with, or along, the base body portion 11, its subsequent portion corresponding to the curved stent graft holder 14 or the curved stent graft 60, forms a curved portion 44 forming a curved structure along and matching the curve thereof, its further subsequent portion that is connected to the hook and the holding rings forms a flexed portion 45 of the wire 40, its portion following the above flexed portion turns back and similarly forms a curved portion 46 and its portion thereafter again forms a straight-line portion corresponding to the base portion of the dilator and ends at the other end portion 42. The above one end portion 41 is fixed with the wire fixing member 15, and the other end portion 42 is fixed by pinching it in the wire fixing portion (wire fixing notch portion) 43.

More specifically, the wire 40 (flexed portion 45 thereof) is wound around the forward end circumference of the first annular unit 61 (from the insertion direction toward a patient) of the stent graft 60 along the above holding rings 69 as shown in (A) of FIG. 11. (Note: The wire is not completely bound or fixed to the holding rings, so that the wire can move or slide along the rings).

In the above manner, the wire 40 is passed through the above holding rings 67, 68 and 69 and wound around the forward end circumference of the first tubular unit 61 (from the insertion direction toward a patient), and then, the leading and trailing end portions thereof are symmetrically passed through the inside of the stent graft 60 in the longitudinal axis direction as shown in (C) of FIG. 11, FIG. 4 and FIG. 6 (which show states where the wire end portions 41 and 42 are fixed). Then, one end portion 42 of the wire 40 is pinched and fixed in the wire fixing notch portion 43 provided in the forward of front portion of the base body portion 11 of the dilator 10 (FIG. 6), and the other end portion 41 of the wire 40 is led out on the proximal end portion 12 of the dilator, through the concave portion 17 between the outer surface of the dilator 10 and the inner surface of the sheath 30 or the wire lumen 100 formed all the distance from the leading end of the dilator 10 to the proximal end 12 thereof and through the wire withdrawal outlet 9, and secured or fixed with the pinching force of the wire fixing member 15.

In addition, there may be employed a constitution in which the wire 40 (end portion 42) is not so fixed in the wire fixing notch portion 43 as described above but both the wire end portions 41 and 42 are led out onto the proximal end portion 12 of the dilator and fixed with the pinching force of the wire fixing member 15. FIGS. 1 and 5 show a state wherein the end portion 41 of the wire 40 is led out on the proximal end portion 12 side of the dilator 10 and fixed with the wire fixing member 15. Alternatively, the end portion 41 of the wire 40 may be fixed, for example, with a pressure of a plug unit or by means of binding or tying the wire 40.

By any one of the above fixing methods, the wire 40 is so structured to be easily taken out when the wire end portion 41 is pulled out of the wire fixing member 15.

The material for constituting the wire 40 is not specially limited so long as it is a wire having strength and elasticity to some extent. It can be selected from sutures formed of a nylon fiber, a fluorocarbon resin fiber, etc., metals such as a nickel-titanium superelastic alloy, stainless steel, etc., or wires made of plastics, carbon, etc. For example, a nickel-titanium superelastic metal wire having a diameter of approximately 0.1 to 0.3 mm, a twisted stainless steel wire(s) having a diameter of approximately 0.2 to 0.3 mm or a suture having a diameter of approximately 0.1 to 0.2 is suitably used.
(Catheter)

The stent graft indwelling device of this invention can be used with a catheter mounted thereon. The catheter refers to a tube formed of a polyamide, polyurethane, etc., and has a guide wire lumen and a contrast medium lumen, and is connected to the top of the fixed chip 20 when used.

The stent graft indwelling device is generally inserted along a wire (guide wire GW) that is pre-inserted into a body for guiding it along a route (from a brachial artery to a femoral artery through a branchiocephalic arterial trunk, an aortic arc, a thoracic aorta, an abdominal aorta, a common iliac artery and an external iliac artery). If the catheter is connected to the top end of the fixed chip, there exists an advantage that the contact of the above top end to a blood vessel wall is decreased when the stent graft is passed through a curved artery. However, the stent graft indwelling device of this invention can be mostly operated in a diseased part while keeping the top end of the fixed chip free from or off a blood vessel wall even if the above catheter is not mounted, thereby making it unnecessarily to mount the catheter thereon.
(Fixed Chip)

This invention also has as another feature in that the fixed chip 20 is attached to the forward end of the stent graft holder to adjust the indwelling position and insertion angle of the stent graft 60.

The fixed chip 20 is in principle composed of two pieces such as a base body 21 and a cap 22. More specifically, as shown in FIG. 12 illustrating the base body 21 and the cap 22, FIG. 13 illustrating the base body 21 and FIG. 14 illustrating the cap 22, a hook holding groove or mechanism 26 is formed between the upper opening portion of the base body 21 and the cap 22. Further, a contrast medium ejecting port 27 is formed in the bottom of the base body 21.

In each of FIGS. 12 to 14, (A) is a plan view, (B) is a front view (or longitudinal cross-sectional view), (C) is a bottom view, (D) is a left side view and (E) is a right side view, and (F) in FIG. 12 is a partial enlarged cross-sectional view. As shown in FIG. 14, the cap 22 is composed of a cap sleeve portion 22A and a top portion 28 covering the upper portion of the sleeve portion, and in the bottom of the above sleeve portion 22A is formed an engagement portion 29 to engage with the base body 21. In the sleeve portion 22A, further, a lumen 25 to work as a flow passage for a contrast medium, etc., is formed. The cap 22 is mounted on or attached to the base body 21 by causing the above engagement portion 29 (FIG. 14 shows a projection, while it may be a groove) to engage with an engagement portion (which is not shown, and this may be a groove or projection so long as it can engage with the engagement portion 29) of the base body 22.
(Fixing of Fixed Chip to Stent Graft)

In the fixed chip 20, the forward end portion of the stent graft holder 14 is forced into the lumen 24 of proximal end portion of the base body 21 and the lumen 25 of the cap 22 and passes through these lumens 24 and 25, thereby the fixed chip 20 is mounted on or attached to the top end of the stent graft holder and the cap 22 also is fixed to the base body 21 of the fixed chip.

In the fixed chip 22 in this invention, as shown in (B) of FIG. 14, the hook holding groove 26 is formed extending from the upper surface (front surface) of the fixed chip 20 and in the center direction nearly perpendicular to a tangent line on the outer circumference (circumference) of the fixed chip 20. Due to the above structure, when the stent graft 60 is housed or accommodated in the sheath 30, it is converged or compressed in the base portion of the hook 66, so that the stent graft 60 in no case comes off the fixed chip 20.

As will be described later, when the release of the stent graft 60 is completed, the tension of the wire does not work any more, and the base portion of the hook 66 expands together, so that the hook 66 can be easily removed from the fixed chip 20.

The fixed chip 20 in this invention, composed of at least two parts (base body 21 and cap 22) in combination, thereby the hook holding groove of mechanism 26 can be constituted three-dimensionally, and stably in form.

A conventional fixed chip having a one-piece structure is produced by a non-molding, one-by-one method in which rods having an outer diameter nearly equivalent to that of a dilator having a guide wire lumen have been processed by melt-processing or grinding. In contrast thereto, the fixed chip in this invention can be produced much more easily by injection molding.

(Assembly of Indwelling Device and Loading of Stent Graft)

One example of the method of assembling (producing) the stent graft indwelling device of this invention will be explained below.

(1) As already described, the wire 40 is passed through the stent graft 60 as shown in FIG. 11, and the wire 40 is fixed to the wire fixing member 15.

(2) The dilator 10 having the base body portion 11 and the stent graft holder 14 is inserted into the sheath 30 in advance. In this case, the dilator 10 may be inserted in a manner in which the proximal end portion of the base portion 11 enters the opening portion positioned in the forward end of the sheath 30 (large-diameter portion 39), or the dilator may be inserted in a manner in which the stent graft holder 14 enters the proximal end portion of the sheath 30.

(3) The proximal end portion (an opposite side to the insertion direction toward a patient) of the stent graft 60 shown in FIG. 9 is diameter-decreased (compressed in the radial direction) by means of a dedicated folding tool or device, then inserted, inch-by-inch, with great care not to entail twist, into the sheath 30 through the leading end (large-diameter portion 39) of the sheath 30 and fitted to the stent graft holder 14, which was pre-inserted into the sheath as described in above (3).

(4) When the insertion of the stent graft 60 into the sheath 30 is completed, the hook portion 66 forming the forward end thereof is hooked to or into the hook holding groove 26 of the fixed chip 20 and then the fixed chip 20 is secured to the leading end of the stent graft holder 14 and fixed with the leading end of the sheath 30 (large-diameter portion 39) to complete the loading of the stent graft.

(5) The stent graft indwelling device in which the stent graft 60, the fixed chip 20 and the wire 40 are loaded or fixed is encased in a proper packaging material and sterilized by way of a sterilization method such as ethylene oxide gas sterilization. In the above manner, the preparation for use of the stent graft indwelling device is thus completed.

(Insertion and Indwelling of Stent Graft and Withdrawal of Wire)

FIGS. 15 to 18 are schematic drawings of one embodiment in which the indwelling device of this invention is inserted into a diseased part (blood vessel) and a stent graft is placed or retained there.

Figure 15:
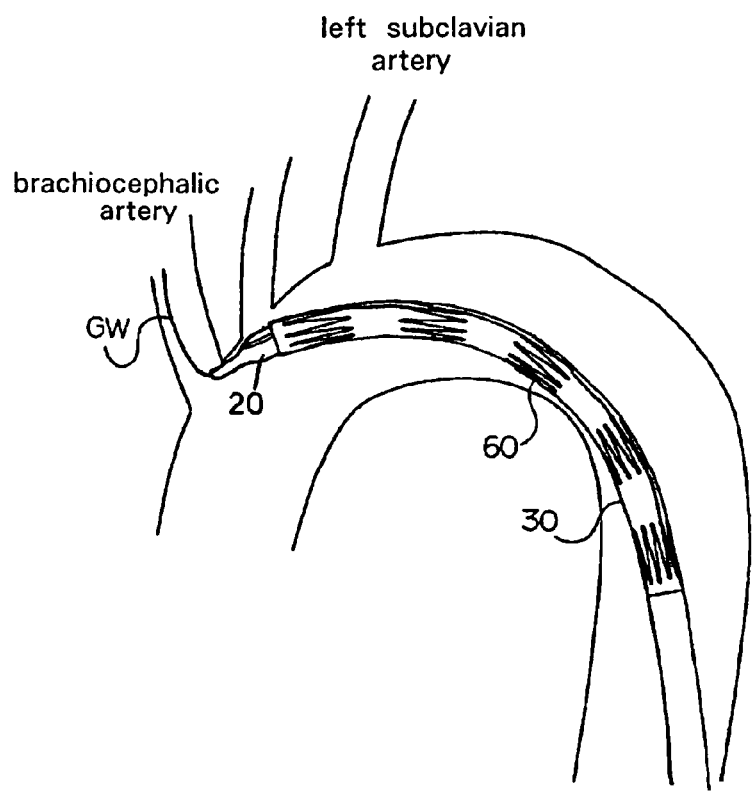
FIGS. 15 to 18 are drawings for explaining an example of the method of handling the stent graft indwelling device of this invention.

As shown in FIG. 15, the sheath 30 loaded with the stent graft 60 is delivered or transported to a targeted site along the guide wire GW that is pre-inserted as a guide or rail up to a diseased part (blood vessel) where placement or indwelling of the stent graft 60 is to made, thereby to be inserted in the targeted diseased part (blood vessel). As shown in FIG. 4, the guide wire GW is inserted through the lumen 16 that passes through the center of the base body portion 11 of the dilator 10.

In this state, the sheath 30 is drawn backward (direction opposite to the diseased part) to expand the first tubular unit 61 inside the diseased part (blood vessel) while the stent graft 60 is pushed outward.

Figure 16:
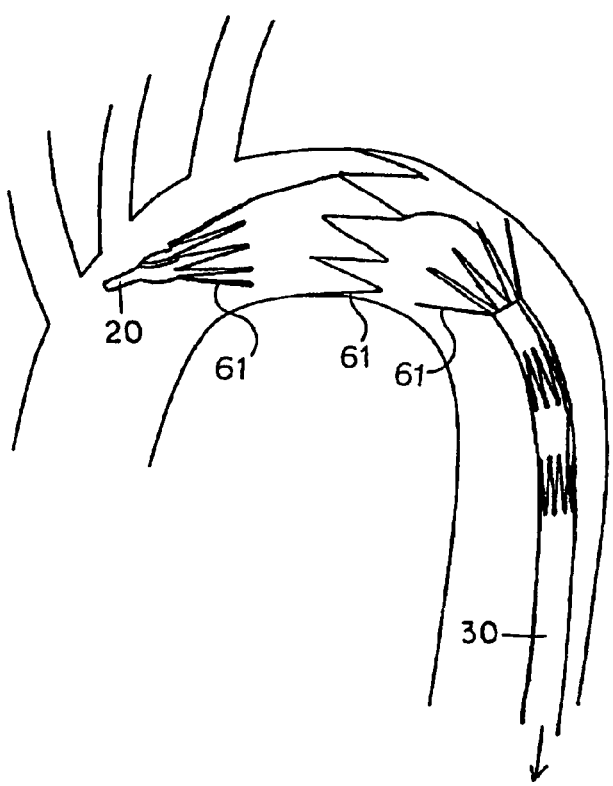

As shown in FIG. 16, the sheath 30 is further drawn backward (direction opposite to the diseased part) to release the second, third, . . . , tubular units 61 inside the diseased part (blood vessel), and the positioning thereof is made.

The curvature of the stent graft 60, placed in the curved portion of a blood vessel, can be even more enhanced accordingly, by adjustment together with the tension on the stent graft 60 and the forces of a blood flow and blood pressure.

In a state where the stent graft 60 is loaded in the sheath 30, no tension works on the wire 40. And, the stent graft 60 is in a state where it is contracted or compressed and folded inside the sheath, and the wire 40 is wound around the forward end of the stent graft 60. When the sheath 30 is drawn backward to release the stent graft 60 in the diseased part as described above, the wire 40 comes into a state of under tension.

More specifically, when the sheath 30 is drawn backward, the wire 40 is extended (tensioned) with the holding rings 67 and 68 being fulcrums, so that the fixed chip 20 on the forward end of the stent graft 60 is pulled toward a smaller curved side, and that, when the stent graft 60 is released to the diseased part from the sheath 30, the stent graft 60 can be so tensioned as to increase or intensify its curvature.

As shown in FIG. 16, therefore, the leading end of the stent graft 60 is released not in full-expansion (for example, when the stent graft has a diameter of 34 mm, the first tubular unit 61 is half opened with a diameter of approximately 20 mm), and even when the remaining second, third . . . tubular units 61 are released in a blood vessel, it does not immediately occur that the tubular units 61 are completely expanded and fixed in the blood vessel. Therefore, the adjustment of the indwelling or placement site and insertion angle of the stent graft 60 can be easily made by adjusting the position of the sheath 30 and the tension of the wire 40.

Figure 17:
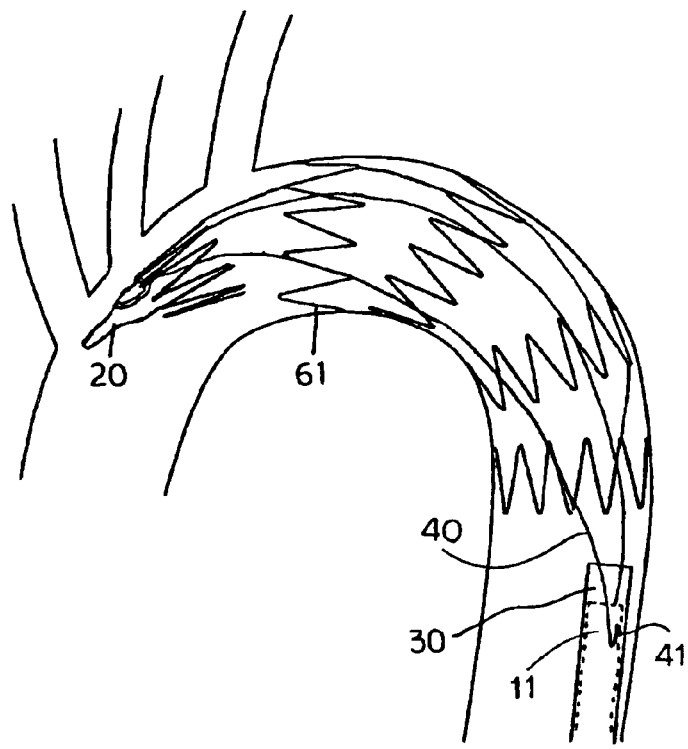

With respect to the determination of the position of the inserted stent graft 60 following procedure is made. The indwelling site and insertion angle of the stent graft 60 is first confirmed with an X-ray fluoroscope by ejecting a contrast medium from the contrast medium ejecting port 27 of the fixed chip 20 arranged at the forward end of the stent graft 60 through the lumen 16 (contrast medium injection passage, guide wire lumen) of the dilator 10, and then the third tubular unit 61 and the tubular units thereafter can be released while finely adjusting the angle and indwelling site for accurate insertion of the stent graft 60 in a diseased part. FIG. 17 shows a state where all the tubular units of the stent graft have been released in the above manner.

When the entire stent has been released from the sheath 30 as described above, no tension works on the wire 40 any more that the hook portion 66 of the stent graft is released from the hook holding groove or mechanism 26 of the fixed chip 20, and thereby the placement or indwelling of the stent graft 60 is completed.

After completion of the restraining of the stent graft 60, an operator of the indwelling device draws the wire end portion 41 of the wire 40 through wire fixing member 15 under his or her hand, thereby the wire 40 can be withdrawn from the stent graft indwelling device.

In the indwelling device of this invention, the wire 40 is passed symmetrically through the holding rings 67, 68 and 69, one end portion 41 of the wire 40 is fixed in the wire fixing member 15, and the other end portion 42 is fixed by pinching it in the wire fixing portion 43 (i.e., wire fixing notch portion 43) on the fore circumference of the dilator 10, so that the wire 40 can be easily withdrawn from the indwelling device after completion of the placement of the stent graft 60.

INDUSTRIAL UTILITY (A) the stent graft indwelling device of this invention has the following features.

(1) In the stent graft indwelling device of this invention, when the stent graft 60 is released from the sheath 30, the wire 40 comes to be applying tension on the stent graft 60 to be released, thereby fine adjustment or the insertion angle and indwelling site can be made in a blood vessel while the stent graft 60 is in a semi-expansion or not completely expanded state.

(2) In the stent graft indwelling device of this invention, the stent graft 60 can be released into a blood vessel in a state wherein the curvature of the stent is enhanced (toward a greater curvature) while decrease in length thereby even in the blood vessel with great curvature, smooth placement of the stent graft 60 can be made following the curved wall of a blood vessel along the curvature.

(3) In the stent graft indwelling device of this invention, the leading end of the sheath 30 and the center side of the stent graft 60 can be free from a blood vessel wall by utilizing or harnessing the expansion power of the stent graft 60 per se while the stent graft 60 is released, thereby reducing the damage of the blood vessel and preventing the disengagement of a thrombolic substance from the blood vessel wall during the maneuver of placing the stent graft.

(B) Further, since the fixed chip 20 to be mounted on the dilator in this invention has a two-piece structure composed of the base body 21 and the cap 22, the hook holding groove or mechanism can be constituted three-dimensionally thus providing the following features.

(1) The fixed chip 20 can be manufactured on a large-scale with high form-reproducibility.

(2) (i) (A case where tension is exerted on the stent graft with the wire 40)

In the fixed chip 20 of this invention, when the stent graft 60, with tension on it, is housed in the sheath 30, the hook 66 on the leading end of the stent graft 60 in no case comes off from the fixed chip 20, and upon releasing the trailing end portion of the stent graft 60 out of the sheath 30, the tension of the wire is reduced or lost, thereby the hook 66 can be detached easily.

(ii) (A case where wire 40 is not used)

In the fixed chip of this invention, when the stent graft 60 is housed in the sheath 30 without wire 40, the hook 66 on the leading end of the stent graft 60 in no case comes off from the fixed chip, and when the trailing end portion of the stent graft 60 is released out of the sheath 30, the hook 66 can be easily detached.

(3) In the fixed chip of this invention, the tubular (pipe-like) stent graft holder 14 passes through the two parts (base body 21 and cap 22) which are bonded and/or fitted to each other, thereby securing the two parts and the cap 22 does not fall off the base body 21. In these points, this invention makes a great contribution to above prior art and has remarkably high industrial utility.

The stent graft indwelling device and the fixed chip of this invention make great contributions over the above-described prior art and have remarkably high industrial utility.

The invention claimed is:

1. A stent graft indwelling device, comprising:
a dilator having a stent graft holder, the stent graft holder holding a stent graft;
a sheath in which is loaded the stent graft held on said stent graft holder of said dilator; and
an adjusting section configured to adjust the insertion angle and adjust an indwelling site of said stent graft when said stent graft is released from said sheath for indwelling, the adjusting section including,
an adjusting wire having a flexed portion and two straight portions, the flexed portion being U-shaped, and the two straight portions being adjacent to each other and extending in a same direction away from the flexed portion, and
an adjusting fixed chip attached to the stent graft holder at a forward end portion of the stent graft holder,
wherein said stent graft is connected to the adjusting wire, and the stent graft is hooked to said adjusting fixed chip,
said stent graft indwelling device is configured to release the stent graft when the stent graft is to be placed, said adjusting wire and said adjusting fixed chip being configured to be released together from the sheath,
said stent graft indwelling device is configured to make adjustments of the insertion angle and indwelling position or site of the stent graft, when said stent graft is released from said sheath of said stent graft indwelling device, for positioning the stent graft by using said adjusting wire and adjusting fixed chip, and said stent graft is configured to become flexed by expansion power of the stent graft making the adjusting fixed chip detached from the wall of a blood vessel with a thrombus,
said adjusting fixed chip includes a base body, a cap, and a hook holding groove, the hook holding groove is formed between said cap and an upper opening portion of the base body, and said hook holding groove is hooked to a hook portion of the stent graft, and
the forward end portion of the stent graft holder is configured to be forced into a lumen at a proximal end portion of said adjusting fixed chip base body and into a lumen of the cap so said forward end portion of the stent graft holder is passed through the lumen of the adjusting fixed chip base body and the lumen of the cap in order to fix the cap and the base body together.

2. A stent graft indwelling comprising
a dilator having a stent graft holder, the stent graft holder holding a stent graft;
a sheath in which is loaded the stent graft held on said stent graft holder of said dilator; and
an adjusting section configured to adjust the insertion angle and adjust an indwelling site of said stent graft when said stent graft is released from said sheath for indwelling, the adjusting section including,
an adjusting wire having a flexed portion and two straight portions, the flexed portion being U-shaped, and the two straight portions being adjacent to each other and extending in a same direction away from the flexed portion, and an adjusting fixed chip attached to the stent graft holder at a forward end portion of the stent graft holder, wherein said stent graft is connected to the adjusting wire, and the stent graft is hooked to said adjusting fixed chip, said stent graft indwelling device is configured to release the stent graft when the stent graft is to be placed, said adjusting wire and said adjusting fixed chip being configured to be released together from the sheath, said stent graft indwelling device is configured to make adjustments of the insertion angle and indwelling position or site of the stent graft, when said stent graft is released from said sheath of said stent graft indwelling device, for positioning the stent graft by using said adjusting wire and adjusting fixed chip, and said stent graft is configured to become flexed by expansion power of the stent graft making the adjusting fixed chip detached from the wall of a blood vessel with a thrombus, said dilator has a base body portion, and a fluid passage is formed along a side face of said base body portion, said adjusting section includes the base body portion of said dilator, the stent graft holder, an adjusting wire fixing member mounted on a proximal end portion of the dilator, a hook portion, hook-portion holding rings, and circumference holding rings that are formed on a forward end of a first tubular unit, the adjusting wire extends either from said holding rings through a portion between the dilator and the sheath or through a wire lumen, extends through a wire withdrawal outlet, and is fixed to said adjusting wire fixing member, and the wire lumen is formed from a forward end of the dilator to a proximal end portion of the dilator.

3. A stent graft indwelling device, comprising:

a dilator having a stent graft holder, the stent graft holder holding a stent graft;

a sheath in which is loaded the stent graft held on said stent graft holder of said dilator; and an adjusting section configured to adjust the insertion angle and adjust an indwelling site of said stent graft when said stent graft is released from said sheath for indwelling, the adjusting section including, an adjusting wire having a flexed portion and two straight portions, the flexed portion being U-shaped, and the two straight portions being adjacent to each other and extending in a same direction away from the flexed portion, and an adjusting fixed chip attached to the stent graft holder at a forward end portion of the stent graft holder, wherein said stent graft is connected to the adjusting wire, and the stent graft is hooked to said adjusting fixed chip, said stent graft indwelling device is configured to release the stent graft when the stent graft is to be placed, said adjusting wire and said adjusting fixed chip being configured to be released together from the sheath, said stent graft indwelling device is configured to make adjustments of the insertion angle and indwelling position or site of the stent graft, when said stent graft is released from said sheath of said stent graft indwelling device, for positioning the stent graft by using said adjusting wire and adjusting fixed chip, and said stent graft is configured to become flexed by expansion power of the stent graft making the adjusting fixed chip detached from the wall of a blood vessel with a thrombus, an adjusting wire fixing member is mounted on a proximal end portion of said dilator, and a proximal end portion of the adjusting wire is configured to be unfixed from said adjusting wire fixing member and drawn out of a hook-portion holding ring and circumference holding rings of said stent graft so the adjusting wire can be drawn out of said stent graft indwelling device.

* * * * *

UNITED STATES PATENT AND TRADEMARK OFFICE
CERTIFICATE OF CORRECTION

PATENT NO. : 8,137,393 B2  
APPLICATION NO. : 11/578287  
DATED : March 20, 2012  
INVENTOR(S) : Shin Ishimaru et al.

Page 1 of 1

It is certified that error appears in the above-identified patent and that said Letters Patent is hereby corrected as shown below:

On the title page, Item (86), the Application Filing Date is incorrect. Item (86) should read:

-- (86) PCT No.: PCT/JP2005/007737

§ 371 (c)(1),  
(2), (4) Date: Jan. 5, 2007 --

Signed and Sealed this  
Twenty-fifth Day of March, 2014

Michelle K. Lee  
*Deputy Director of the United States Patent and Trademark Office*